(12) United States Patent
Makhnejia et al.

(10) Patent No.: US 11,617,501 B2
(45) Date of Patent: Apr. 4, 2023

(54) LIGHT CABLE CAP AND METHOD OF USING THE SAME

(71) Applicant: GEORGIA TECH RESEARCH CORPORATION, Atlanta, GA (US)

(72) Inventors: Kamil Makhnejia, Atlanta, GA (US); James K. Rains, Marietta, GA (US); Patrick William Strane, Atlanta, GA (US); Lance Michael Black, Pearland, TX (US)

(73) Assignee: Georgia Tech Research Corporation, Atlanta, GA (US)

( * ) Notice: Subject to any disclaimer, the term of this patent is extended or adjusted under 35 U.S.C. 154(b) by 126 days.

(21) Appl. No.: 16/485,238

(22) PCT Filed: Feb. 16, 2018

(86) PCT No.: PCT/US2018/018506
§ 371 (c)(1),
(2) Date: Aug. 12, 2019

(87) PCT Pub. No.: WO2018/152409
PCT Pub. Date: Aug. 23, 2018

(65) Prior Publication Data
US 2019/0365216 A1   Dec. 5, 2019

Related U.S. Application Data

(60) Provisional application No. 62/459,931, filed on Feb. 16, 2017.

(51) Int. Cl.
*A61B 1/12* (2006.01)
*A61B 1/00* (2006.01)
*A61B 1/07* (2006.01)

(52) U.S. Cl.
CPC .......... *A61B 1/128* (2013.01); *A61B 1/00126* (2013.01); *A61B 1/00137* (2013.01); *A61B 1/07* (2013.01)

(58) Field of Classification Search
CPC . A61B 1/128; A61B 1/00126; A61B 1/00137; A61B 1/07; A61B 1/00165;
(Continued)

(56) References Cited

U.S. PATENT DOCUMENTS 5,549,594 A * 8/1996 Brunken ............ A61B 1/00137
606/1
5,709,668 A * 1/1998 Wacks ................ A61M 5/2033
222/326

(Continued)

FOREIGN PATENT DOCUMENTS

CN     203417184      2/2014
JP     07191266 A  *  7/1995
(Continued)

OTHER PUBLICATIONS

Assael et al., Thermal Conductivity of Polymethyl Methacrylate (PMMA) and Borosilicate Crown Glass BK7, Sep. 2005 International Journal of Thermophysics, vol. 26, No. 5, pp. 1595-1605. (Year: 2005).*

(Continued)

*Primary Examiner* — Aaron B Fairchild
*Assistant Examiner* — Stephen Floyd London
(74) *Attorney, Agent, or Firm* — Meunier Carlin & Curfman LLC

(57) ABSTRACT

A medical device reduces the risk of operating room fires caused by light sources by shielding the illuminated light cable from directly interacting with surgical drapes or patient skin. The device includes a silicone housing that mates circumferentially over existing endoscopic light (Continued)

cables and a thermal insulator can be positioned over the light emitting tip of the cable.

22 Claims, 12 Drawing Sheets

(58) Field of Classification Search
CPC ...... G02B 6/262; G02B 6/0093; G02B 6/245; G02B 6/3849; G02B 6/387; G02B 6/443; G02B 6/4436; G02B 6/4486; G02B 2006/4297; A61M 5/1626; A61M 5/3202; A61M 25/0618; F21V 15/012; F21V 15/015; F21V 15/04; B65D 41/22; B65D 41/58; B65D 41/60; B65D 45/32; B65D 45/327; B65D 47/0823; B65D 53/02; B65D 53/04

See application file for complete search history.

(56) References Cited

U.S. PATENT DOCUMENTS

| | | | | |
|---|---|---|---|---|
| 6,280,102 | B1* | 8/2001 | Go | G02B 6/421 385/94 |
| 6,612,750 | B1 | 9/2003 | Bull et al. | |
| 7,991,260 | B2* | 8/2011 | Doody | G02B 6/4296 385/139 |
| 2002/0065450 | A1* | 5/2002 | Ogawa | A61B 1/126 600/157 |
| 2004/0171283 | A1* | 9/2004 | Ngo | G02B 6/3849 439/55 |
| 2006/0037977 | A1* | 2/2006 | Eimer | B65D 47/2031 222/494 |
| 2006/0204200 | A1 | 9/2006 | Lampert et al. | |
| 2006/0255093 | A1* | 11/2006 | Wimroither | B23K 9/1735 228/101 |
| 2008/0249478 | A1* | 10/2008 | Ishikura | A61M 25/0618 604/198 |
| 2008/0317428 | A1* | 12/2008 | Nakagawa | G02B 6/4296 385/139 |
| 2010/0310226 | A1* | 12/2010 | Wakileh | G02B 6/3849 385/139 |
| 2011/0034774 | A1 | 2/2011 | Doody et al. | |
| 2013/0131453 | A1* | 5/2013 | Imai | A61B 1/00094 600/156 |
| 2014/0163470 | A1* | 6/2014 | Baid | A61M 25/0618 604/164.08 |
| 2015/0277063 | A1* | 10/2015 | Hikosaka | G02B 6/428 385/139 |
| 2015/0297063 | A1* | 10/2015 | Wolcott | A61B 1/00068 600/158 |
| 2016/0128755 | A1* | 5/2016 | Ho | A61B 18/042 606/41 |
| 2016/0259131 | A1* | 9/2016 | Erdman | G02B 6/3866 |
| 2016/0324402 | A1* | 11/2016 | Yajima | G02B 6/3897 |
| 2019/0208998 | A1* | 7/2019 | Powers | A61B 1/00186 |
| 2019/0357761 | A1* | 11/2019 | Hessler | A61C 9/004 |

FOREIGN PATENT DOCUMENTS

| | | |
|---|---|---|
| JP | H07191266 | 7/1995 |
| JP | 4406130 B2 * | 1/2010 |
| WO | 2017/146910 | 8/2017 |

OTHER PUBLICATIONS

Mu, Qiuhong et al., Thermal Conductivity of Silicone Rubber Filled with ZnO, 2007, Polymer Composites, p. 125-130. (Year: 2007).*

International Search Report and Written Opinion dated May 16, 2018, from International Application No. PCT/US2018/018506, 7 pages.

Extended EP Search Report dated Nov. 9, 2020, issued in related EP application No. 18754555, 7 pages.

Office Action dated Jul. 5, 2022 in Japanese Application No. 2019-544017 and English translation.

* cited by examiner

LIGHT CABLE CAP AND METHOD OF USING THE SAME

BACKGROUND OF THE INVENTION

Field of the Invention

Embodiments of the present invention relate to a cap for a light source, specifically a light cable used in endoscopic procedures.

Background

Endoscopy is an area of medicine that is rapidly gaining popularity. Primarily used in surgical and diagnostic cases, endoscopy and its variants (e.g. laparoscopy, arthroscopy, cystoscopy, etc.) utilize small incisions externally or natural orifices to access internal anatomies and structures for manipulation. Although endoscopic procedures vary in technique across medical specialties, they all have the same foundation. Due to the decreased levels of infection and extraneous trauma from entry and closure of the surgical site compared to traditional surgeries that involve very large incisions, endoscopic surgeries are becoming the gold standard in medicine.

Despite the growing popularity of the endoscopy market in medicine, there are inherent risks. FIG. 1 illustrates disadvantages of an exposed light source cable 148 in a surgical environment. The light source cable 148 connects to a light source device 154. A camera cable 156 may also be included for various procedures. As described above, the light source device 154 and light cable system 148 are a major component of general endoscopy and are used to convey light to an endoscope 158 for insertion into a patient 160 to the body cavity of interest via various means, such as a trocar 152 or body orifice (not shown). The patient is typically covered by a drape 162. For optimal visualization, the light source is required to have very high intensity. Often times during a procedure, surgeons use more than one scope to improve visualization of the surgical area. As a result, surgeons will exchange scopes at different points during a procedure, and the light cables 148 and their light emitting tip 138 are often left illuminated during scope changes.

Typically, the illuminated light cables 148 are placed on the patient 160 and the drapes 162 during exchanges while the surgical technician prepares the scope 158 and the surgeon continues monitoring the patient 160 and their situation. With the high intensity light still being emitted from the tip 138 of the light cable 148, a large amount of thermal energy is released to the surrounding environment (patient skin and drapes) sometimes resulting in smoking, fires, and burns (FIG. 1). The light tip 138 can reach temperatures on the order of 500° F. Even after the light source 154 has been turned off, the light emitting tip 138 or the disconnected light cable 148 can remain hot for some time. FIG. 1 illustrates both the scope in use with the light cable and the light cable 148 disconnected from the scope to expose the light tip 138 to the ambient environment.

The current solution to this safety issue is for the circulating nurse to physically switch off the light source or put it on standby during scope changes. This protocol is ineffective as the circulating nurse cannot break the sterile field or is often busy charting and assisting surgeons and surgical technicians with other aspects of the surgery.

Accordingly, there is a need for a safe, effective and efficient means for reducing the outward emittance of the thermal energy from the light source to the surrounding environment that acts as fuel for a largely preventable thermal event.

BRIEF SUMMARY OF THE INVENTION

Accordingly, the present invention is directed to a light cable cap that obviates one or more of the problems due to limitations and disadvantages of the related art.

An advantage of the present invention is to provide a cap for a light source cable. The cap has a housing including a ring, a shield and a bridge, the bridge extending from the ring to the shield, the shield being movable from a first position to a second position; and a thermal insulator in the shield.

The light cable cap may include a silicone housing that mates mostly circumferentially over existing endoscopic light cables and a thermal insulator can be positioned over the light emitting tip of the cable.

In another aspect of the present invention a method of using a scope with a light source cable, the light source cable including a light cable cap having a ring, a shield, a bridge and a thermal insulator in the shield, the shield adjacent to a light emitter of the light source cable comprises displacing the shield away from an axial direction of the light cable cap; connecting the scope to the light source cable; and releasing the shield. The method may further include disconnecting the scope from the light source cable; and allowing the shield to rebound to an original position adjacent the light emitter. The method may also include manually repositioning the shield over the light emitter.

Further embodiments, features, and advantages of the light cable cap, as well as the structure and operation of the various embodiments of the light cable cap, are described in detail below with reference to the accompanying drawings.

It is to be understood that both the foregoing general description and the following detailed description are exemplary and explanatory only, and are not restrictive of the invention as claimed.

BRIEF DESCRIPTION OF THE DRAWINGS

The accompanying figures, which are incorporated herein and form part of the specification, illustrate the light cable cap for endoscopic procedures. Together with the description, the figures further serve to explain the principles of the light cable cap described herein and thereby enable a person skilled in the pertinent art to make and use the light cable cap.

DETAILED DESCRIPTION OF THE INVENTION

Figure 1:
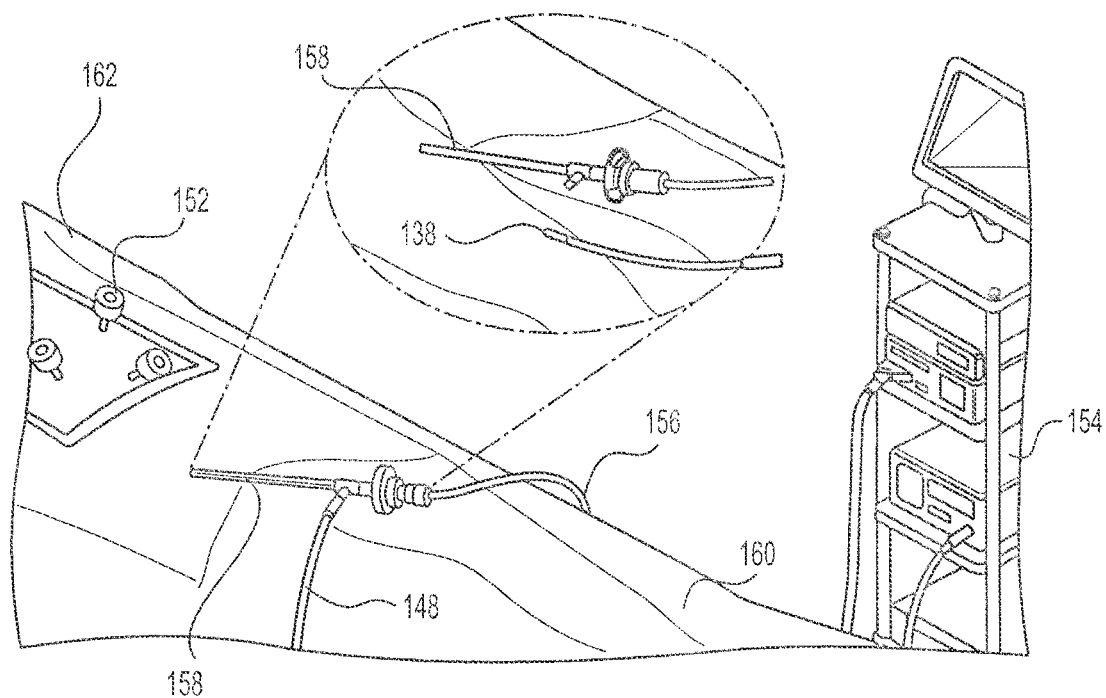
FIG. 1 illustrates disadvantages of an exposed light source cable.

Reference will now be made in detail to embodiments of the light cable cap with reference to the accompanying figures, in which like reference numerals indicate like elements.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Figure 2A:
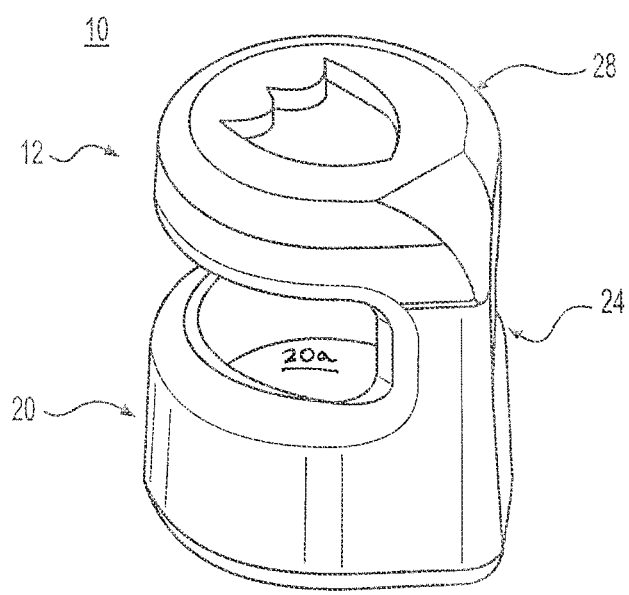
FIG. 2A is an isometric illustration of an embodiment of a light cable cap according to principles of the present invention.

FIG. 2A illustrates an isometric view of an embodiment of a light cable cap 10 according to principles of the present invention. As illustrated in FIG. 2A, the light cable cap 10 has a generally cylindrical profile. The profile may vary from cylindrical as appropriate for adapting to a particular light source device (not shown), including, for example, without limitation, rectangular, oval, hourglass. The light cable cap 10 may further include finger grooves with respect to its outer profile. For example, and as may be imagined from the illustration, the light cable cap 10 itself may have a slightly tapered (frustoconical) profile. Having a cylindrical or slightly tapered, the light cable cap 10 illustrated has a roughly circular cross section, but may have a cross-section as appropriate for adapting to a particular light source device (not shown). The tapered profile may facilitate manufacture of the device by injection molding. An inner profile of the light cable cap 10 will be a shape to sufficiently fit onto a light cable, such as circular. The internal surface of the light cable cap 10 may have an internal surface roughness, at least in the region where the ring is mated to the light cable, to ease installation of the light cable cap 10 onto the light cable 48.

The light cable cap 10 includes two components: a housing 12 that mates over an existing light source (not shown), such as the light tip (not shown) of an endoscopic light cable (not shown), and a thermal insulator 16 that can be positioned over the light emitting tip (not shown) of the light source/cable (not shown), as illustrated in FIGS. 2A-2F. The thermal insulator 16 together with the housing 12 provide a light shield for the light source cable (not shown) that substantially diminishes the thermal and optical energy that escapes to the surrounding environment from the light source cable and light emitting tip (not shown). Although not shown, a heat sink may be used in place of the thermal insulator.

The housing 12 includes a material that provides thermal insulation at least in the location of the thermal insulator 16. In one embodiment, the housing 12 is medical grade silicone, but may be made of other suitable materials, such as a thermoplastic elastomer or rubbers, like Viton or of multiple materials. Other materials include blends such as glass-filled silicones. Without limitation, such material may include Fluorocarbon or Perfluorocarbon rubber; Ethylene Propylene Diene Monomer (EPDM) rubber; neoprene; Nitrile. As illustrated in FIGS. 2A-2F, the housing 12 includes a ring/ring portion or cuff 20, a bridge/bridge portion 24 and a shield/shield portion 28. As can be seen in FIGS. 2A-2F, the shield portion 28 is connected to the ring portion 20 by the bridge portion 24. In the illustrated embodiment, at least the ring portion 20 of the housing 12 comprises a flexible material, such as silicone, allowing the ring portion 20 to be fitted over the end of the light source cable (not shown) such that the interior of the ring portion 20 abuts the light source cable (not shown) at an area that does not emit light and is held in place by friction fit. While friction fit is illustrated, the housing 12 may be held in place by other known methods, including interference fit, temporary adhesive or other known methods. The light cable cap 10 mates mostly circumferentially over existing endoscopic light cables, e.g. the ring/cuff may have a "C" shaped cross section that surrounds most of the circumference of the light tip. The bridge portion 24 may comprise a flexible material, and may be unitary with the ring portion 20, e.g., formed together with the ring portion 20 in an injection molded process. Although not illustrated, the light cable cap 10 may include multiple bridges or multiple articulation points for facilitating movement of the shield away from the light emitting tip and returning it over the light emitting tip when the scope is removed. The "transplacing" of the light cable cap components for attachment to the scope can be performed by the appropriate mechanical movement, as described in more detail in the illustrated embodiments. The housing may include portions (the ring or shield or a hinged bridge) that are not very flexible or are stiff/rigid, e.g., polypropylene (PP), polycarbonate (PC), acrylonitrile butadiene styrene (ABS), polylactic acid (PLA), Thermoplastics, thermosets, etc. Examples of various combinations of rigidity and flexible components is provided below in Table 1.

TABLE 1

| Rigidity options for housing | | | | |
| --- | --- | --- | --- | --- |
| Component | Option #1 | Option #2 | Option #3 | Option #4 |
| Shield | Flexible | Stiff | Flexible | Stiff |
| Bridge | Flexible | Flexible | Flexible | Flexible |
| Ring | Flexible | Flexible | Stiff | Stiff |

As illustrated in FIGS. 2A-2F, bridge portion 24 connects to a periphery of the ring portion 20 and to a periphery of the shield portion 28. The ring portion may extend up almost to the shield portion, as illustrated in FIG. 3, to provide additional thermal protection for a user, i.e., providing more light cable cap surface area for a user to touch and hold. As shown in FIG. 2A, the ring includes an opening 20a in which and/or through which the light source, or light cable with light source, may be passed or fitted.

The purpose of the bridge portion is to allow the user to translate the shield while remaining connected to the light cable. In an embodiment of the present invention, the bridge and the shield portion are made of different materials. In an aspect, the bridge material is same as ring material, but different from thermal insulator material. Material that surrounds the thermal insulator in the shield may be the same material as the bridge portion and ring portion. The present embodiment reduces a number of parts and components and facilitates manufacturing because the bridge and the shield are formed to be unitary in the same the manufacturing process, which may be facilitated by also making the bridge portion and the ring portion from the same material. If a material has a low enough thermal conductivity yet remains flexible and does not degrade at high temperatures, the bridge and shield can both be made of the same material, further simplifying the manufacturing process. If a material is flexible with the capacity to withstand high thermal load, the entire light cable cap (the housing and the thermal insulator) can be made of the same material as one part. Alternatively, the entire shield portion of the device can be a single material with the bridge and ring being another material. The connection between the bridge and shield for this case would be different. Other bridge configurations to achieve the purpose of translating the shield are possible, including a non-unitary bridge portion that articulates with respect to the light cable when the cap is attached to the light cable, an example of which is illustrated in FIG. 12. For example, the variations include a pivoting bridge, a translating bridge, a rotating bridge, etc. That is, the shield portion is movable from a first position over the light tip to a second position away from the light tip, i.e., articulatable from the first position to the second position.

In the present embodiment, the bridge portion flexes to allow the shield to be moved away from the light emitting tip. As a result, the bridge's material should be relatively flexible. For example, Shore A range is estimated to span 30 A to 100 A. For example, 60 A effectively bounces back and is easy to displace during endoscopy attachment. In addition, the bridge can be designed with a thinner cross-section similar to a living hinge to promote flexibility.

In lieu of a full ring that slips over the end of the light cable, embodiments of the presently disclosed light cable cap may include a c-clip, clamp or other fastening device that holds the cap onto a portion of the light cable that allows for the shield member to be translated away from the light emitting tip of the light cable to expose the light emitting tip for providing light to a scope.

Figure 2B:
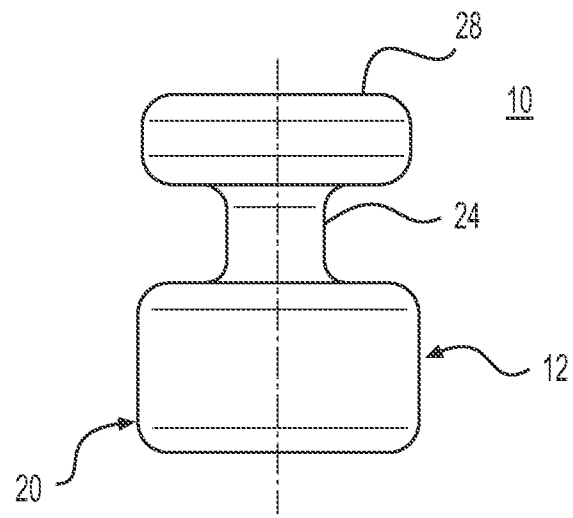
FIG. 2B illustrates a front view of an embodiment of a light cable cap according to principles of the present invention.
Figure 2C:
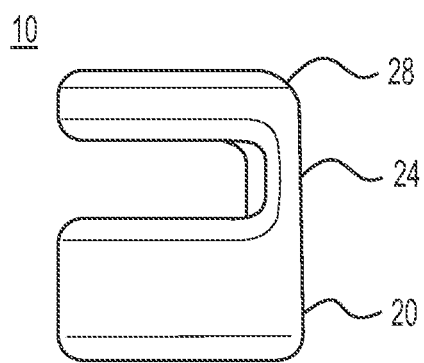
FIG. 2C illustrates a side view of an embodiment of a light cable cap according to principles of the present invention.
Figure 2D:
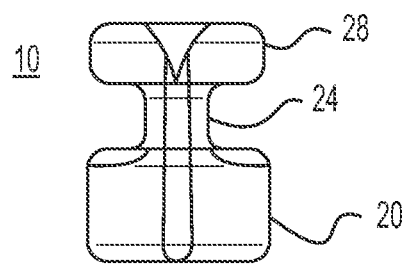
FIG. 2D illustrates a rear view of an embodiment of a light cable cap according to principles of the present invention.
Figure 2E:
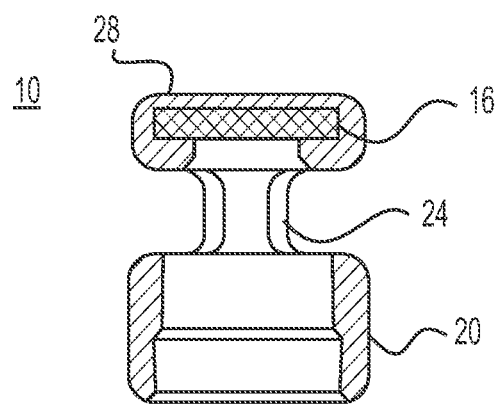
FIG. 2E illustrates a cross-sectional front view of an embodiment of a light cable cap according to principles of the present invention.
Figure 2F:
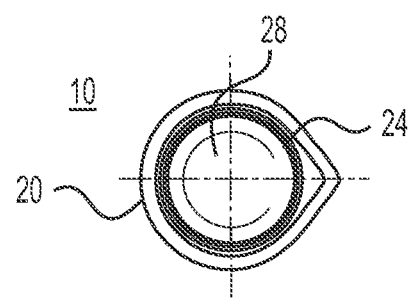
FIG. 2F illustrates a bottom view of an embodiment of a light cable cap according to principles of the present invention.
Figure 3:
FIG. 3 illustrates an embodiment according to principles of the present invention.

FIG. 2B illustrates a front view of a light cable cap 10 according to principles of the present invention. FIG. 2C illustrates a side view of a light cable cap 10 according to principles of the present invention. FIG. 2D illustrates a rear view of a light cable cap 10 according to principles of the present invention. FIG. 2E illustrates a cross-sectional front view of a light cable cap 10 according to principles of the present invention. FIG. 2F illustrates a bottom view of a light cable cap 10 according to principles of the present invention. As illustrated in FIG. 2A-E, the outer sidewall of the light cable cap 10 may have a taper of 3°±1° from the shield portion 28 to an end of the ring portion 20 opposite the shield portion 28. The present embodiment includes a taper to facilitate manufacture by injection molding. A taper is not necessary for the light cable cap and thus the light cable cap profile may be cylindrical, rectangular, oval, hourglass, or other profile, including a varied profile, especially if a clamp or other fastening device is used in place of a ring portion to attach the light cable cap to the light cable, or if the bridge portion is articulated by mechanical pivot, rotation, translation or the like.

As discussed in more detail below, in an endoscopic procedure, one light source cable may be used with different scopes (not shown) at different times during a procedure. The bridge portion 24 or the connection of the bridge portion 24 is sufficiently flexible to allow the shield portion 28 to be displaced from the end of the light source cable (not shown) and pushed away from the scope (not shown) to allow the light source cable (not shown) to provide light to the scope (not shown). When the scope is removed from the light source cable (not shown), resiliency of the material of the bridge portion 24 or the connection of the bridge portion 24 and the shield portion 28 allows the shield portion 28 to return to a position in proximity of light emitting tip 38 (see FIG. 6) of the light cable to fully or partially block the light emitted. In some aspects, the shield portion 28 position may be manually adjusted for a specific placement over the light emitting tip (not shown).

Figure 4:
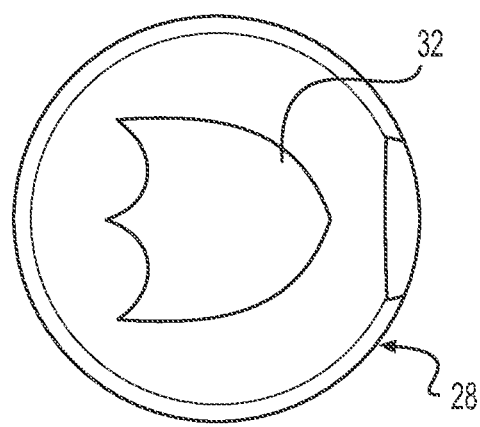
FIG. 4 illustrates a top view of an embodiment of a light cable cap according to principles of the present invention.
Figure 5:
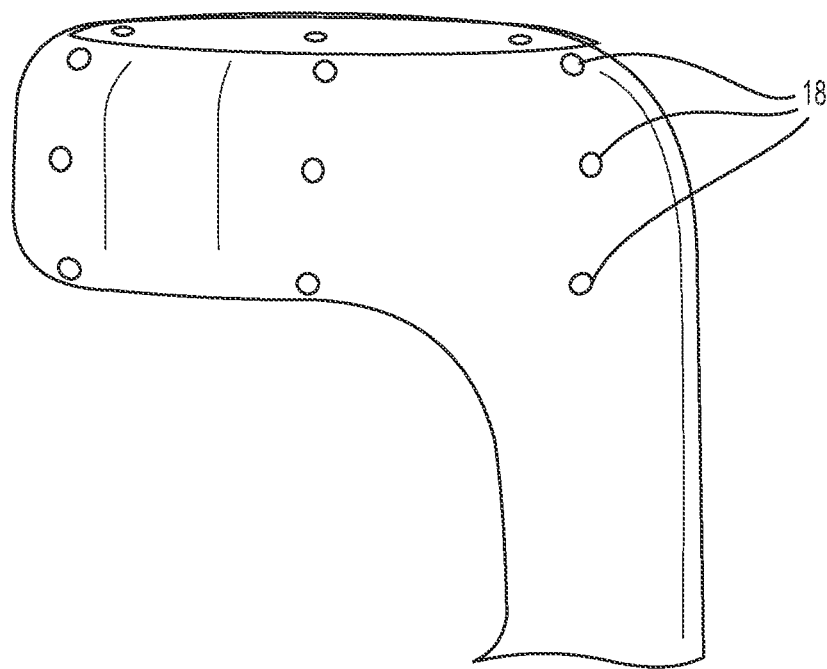
FIG. 5 illustrates an aspect of the present invention to include vent holes for heat dissipation.

FIG. 4 illustrates a top view of a light cable cap 10 according to principles of the present invention. As illustrated in FIG. 4, the shield portion 28 has a generally circular cross-section to mimic the cross-section of the light source cable (not shown). As shown in at least FIGS. 6 and 7, the shield portion 28 may include an orifice or recess 34 into which the light emitting tip 38 extends when the shield portion is positioned over the end of the light cable. The orifice 34 may extend from a surface of the shield intended to receive to the light emitting tip to the thermal insulator 16. Additionally, the orifice/recess 34 may be shaped to accept a light emitting tip 38 of the light source cable end 36 within the orifice/recess, as illustrated in FIG. 6.

As illustrated in FIG. 2E, the shield portion 28 of the housing 12 includes the thermal insulator 16 therein. The shield 28 includes a heat shield/thermal insulator 16 of a high temperature resistant material such as ceramic or glass-filled silicone. Of particular interest, although not required, are glass and ceramic based materials due to their high thermal insulating properties compared to conventional thermoplastics and thermosets. To facilitate direct interaction with the emitted light in some applications, the thermal insulator 16 has low thermal conductivity to withstand elevated temperatures and prevent heat and energy from escaping to the thermally sensitive surroundings. The heat shield/thermal insulator 16 may have a disk shape to facilitate manufacturing and may be of a medical grade ceramic or plastic material that can withstand high temperatures. Exemplary materials for the thermal insulator 16 are Ceramic (e.g., Zirconia, Aluminum Oxide, YTB) or ceramic composite or foam, Vespel polymer, a glass filled silicone material, Viton, Teflon, any glass filled polymers, Polyimide or polyimide-based plastic, Fluoroelastomers or the like. Other suitable materials include metals acting as a thermal conductor or heat sink. The ceramic properties allow for a portion of the light cable cap 10 to be radiopaque, e.g., the radiopaque nature of ceramics may be visible in an x-ray to confirm the presence of the light cable cap 10 in the human body. Other portions of the light cable cap 10 may be made radiopaque for the same purpose. The material of the thermal insulator may be such that it has an internal porosity that is foam-like.

Figure 9A:
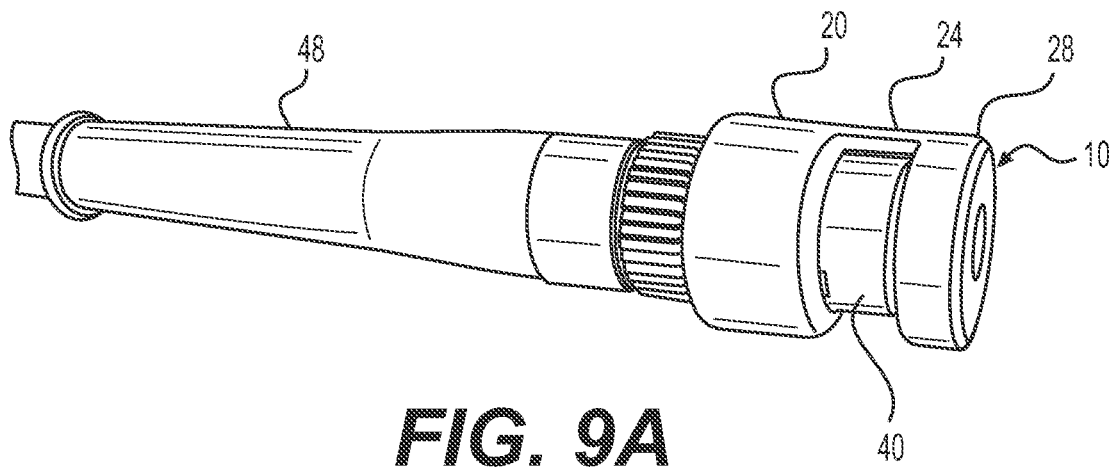
FIGS. 9A-9B illustrate an embodiment of a light cable cap according to principles of the present invention on a light cable.
Figure 9B:
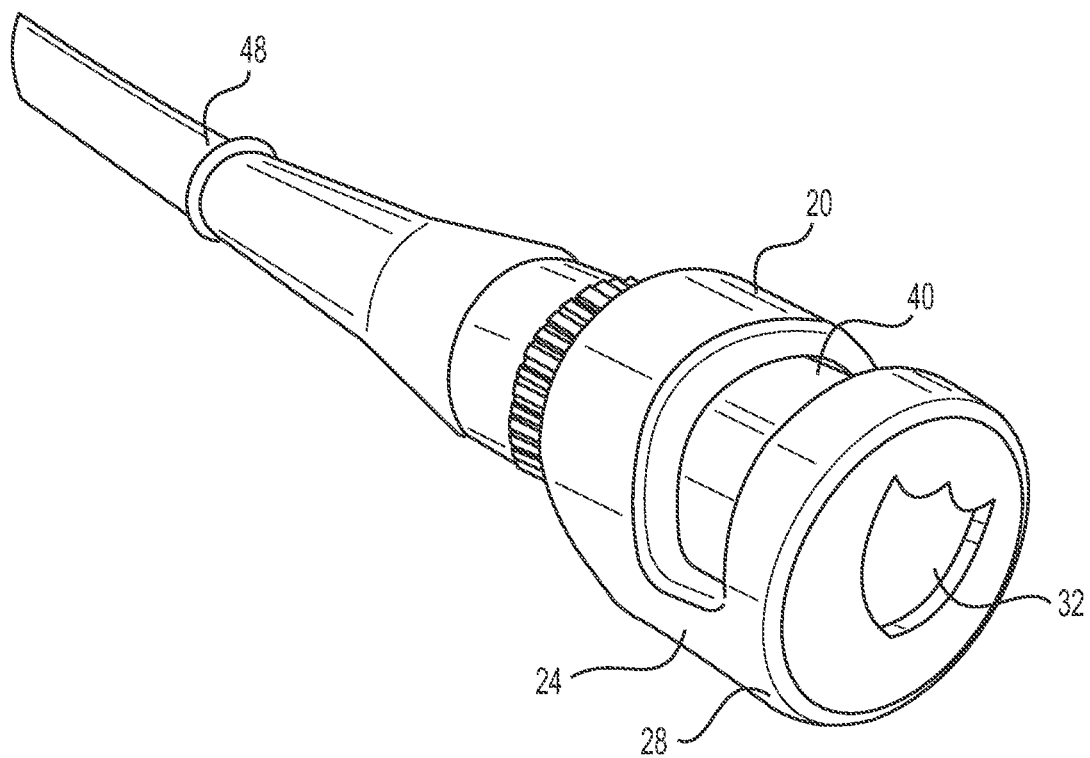
Figure 10A:
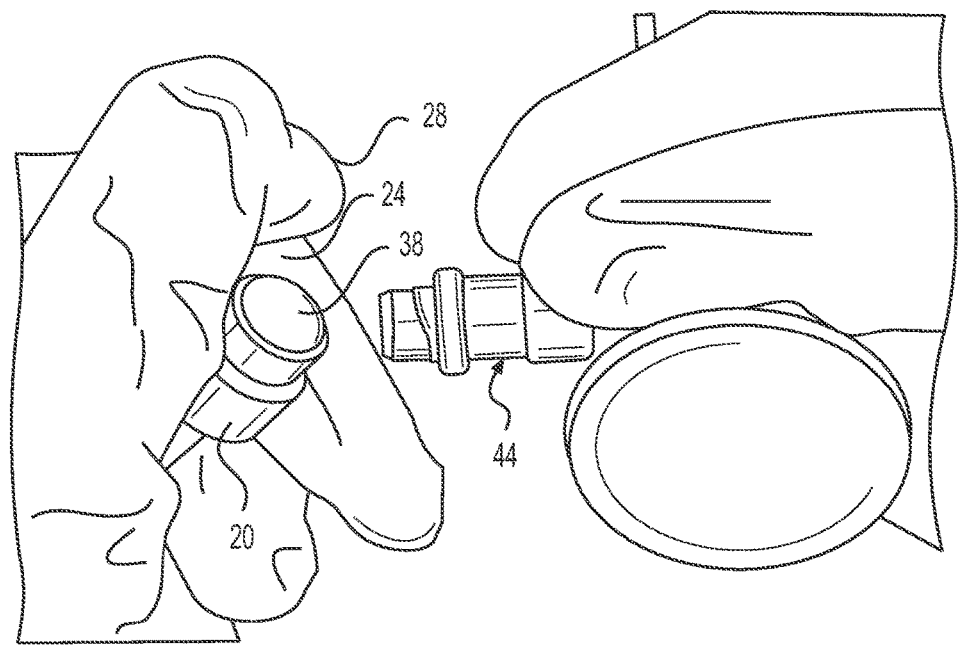
FIGS. 10A-10D illustrate steps of connecting and disconnecting a scope from a light source cable having a light cable cap according to principles of the present invention.
Figure 10B:
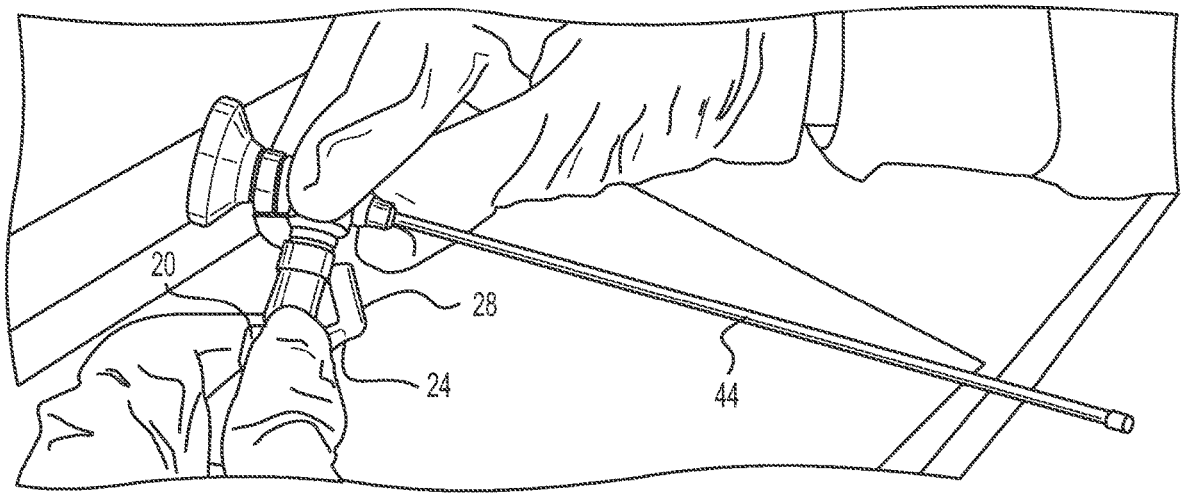
Figure 10C:
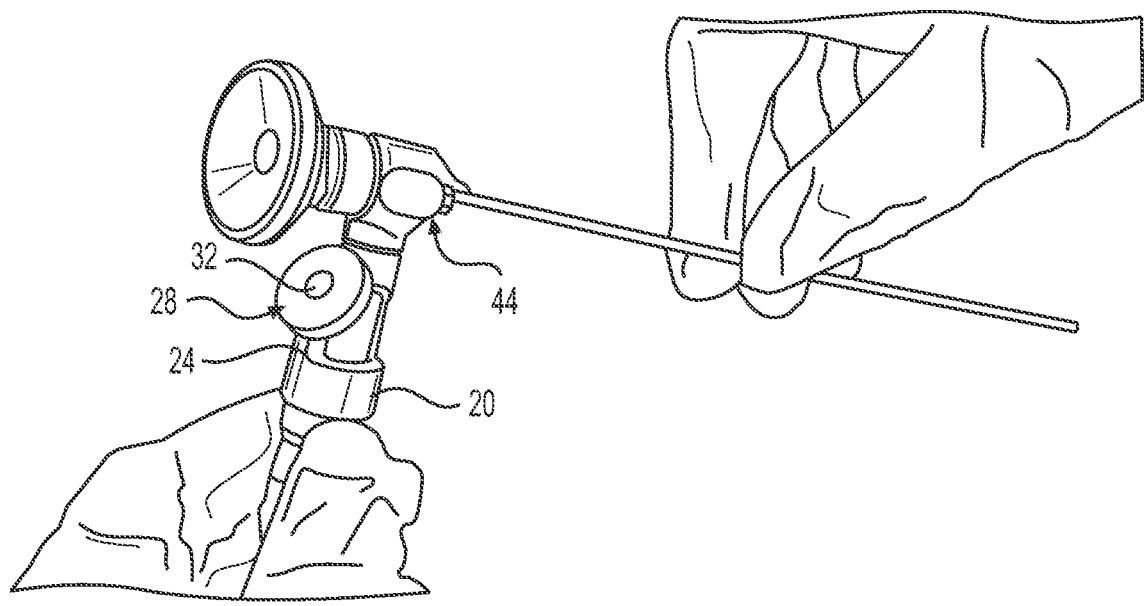

In FIG. 9B or 10C, an additional recess or orifice 32 may extend from the top surface of the shield 28 to the top surface of the thermal insulator 16. Whether or not the recess 32 extends all the way to the thermal insulator 16, the thickness (or reduced thickness in the case of a recess) or orifice allows for some light leakage through the top of the shield to allow the user to see that the light tip is illuminated or not. The housing may also include one or many "vent holes" 18 in the shield portion of the housing to diffuse heat and to assist in overmolding manufacturing of the housing and indication of the heat shield.

Figure 6:
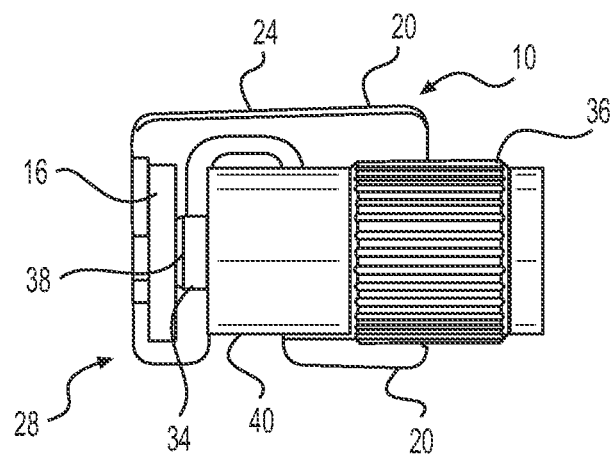
FIG. 6 illustrates a cutaway view of an embodiment of a light cable cap according to principles of the present invention over an exemplary endoscopic light source cable.

FIG. 6 illustrates a cutaway view of the light cable cap 10 according to principles of the present invention over an exemplary endoscopic light source cable 48. As illustrated in FIG. 6, once fitted over the end of the light cable 48, the ring portion 20 extends around a portion of the endoscopic light emitter housing 40 and the bridge portion 24 is adjacent to the light emitter housing 40. The shield portion 28 of the light cable cap 10 with the thermal insulator 16 is adjacent to the light emitting tip 38 of the endoscopic light source. As illustrated in this embodiment, the thermal insulator 16 is directly proximate the light emitting tip 38.

In an embodiment of the present invention, the housing 12 is formed by injection molding such that the ring portion 20, the bridge portion 24 and the shield portion 28 are unitary. The injection molding process may incorporate overmolding the heat shield/thermal insulator 16 such that housing 12 is formed over the heat shield/thermal insulator 16 so that the heat shield/thermal insulator is embedded in the housing 12.

Figure 7:
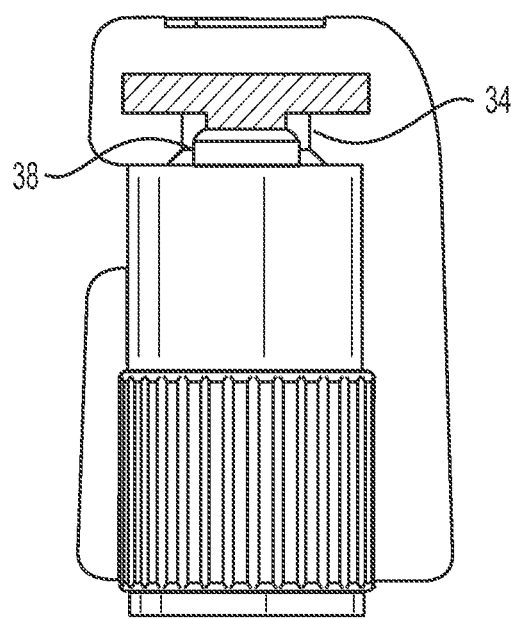
FIG. 7 illustrates a cutaway view of an embodiment of a light cable cap according to principles of the present invention over an exemplary endoscopic light source cable.
Figure 8:
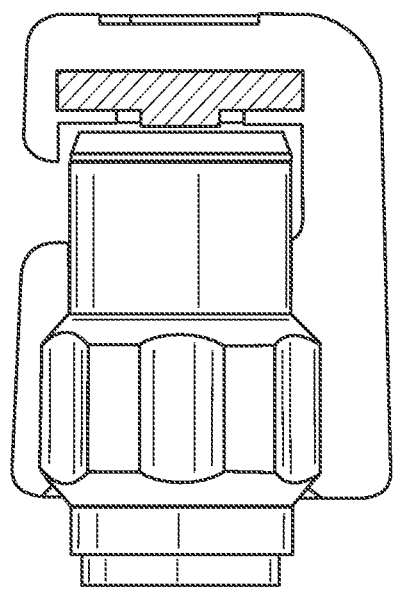
FIG. 8 illustrates a cutaway view of an embodiment of a light cable cap according to principles of the present invention over an exemplary endoscopic light source cable.

FIGS. 7 and 8 illustrate a cutaway view of embodiments of a light cable cap according to principles of the present invention over exemplary "off the shelf" endoscopic light source cables of various manufactures.

FIGS. 9A-9B illustrates a light cable cap according to principles of the present invention on a light cable.

As illustrated in FIGS. 10A-10D, the light cable cap 10 according to principles of the present invention does not have to be disconnected or reconnected between scope changes. (FIG. 10A). In operation, the shield portion 28 is shifted, translated, displaced, hinged, pivoted or otherwise "transplacing", or the like, the shield portion 28 and the bridge portion 24 away from an axial direction of the light cable cap to accommodate connection of a scope 44 to the light source cable 48. (FIG. 10B). The connecting of the scope 44 to the light source cable 48 can be facilitated by rotating the housing 12 along with an adapter on the light source cable 48 for attaching the scope to the light source cable. The light source cable end is typically rotated to secure the connection with the scope instead of rotating the scope to attach the light source cable. Typically, the light source cable end is the portion rotated instead of the scope to reduce the chance of damage to the scope, because of the relatively higher expense of replacing the scope if it were damaged in the process. Once the scope 44 is connected to the light source cable 48, the scope 44 can be used for surgical applications. (FIG. 10C)

Figure 10D:
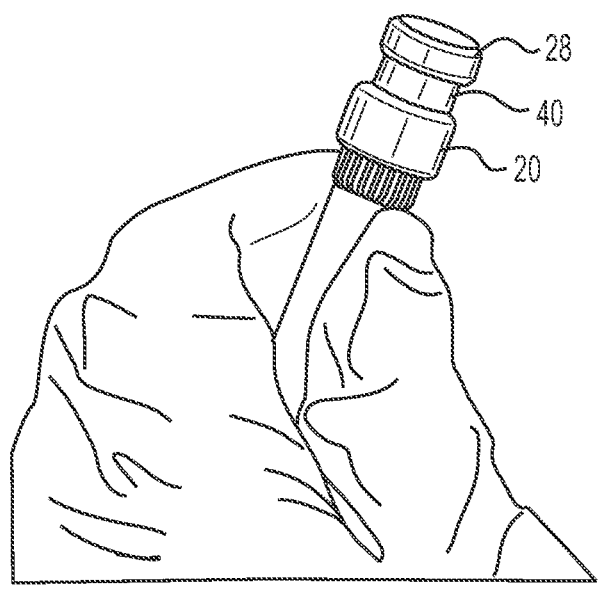

The light cable cap 10 remains paired with the light cable through the entire medical procedure and actively blocks light emitted from a light source that remains illuminated, even during scope changes. It is able to achieve this functional characteristic due to the composition of the housing 12. In the illustrated embodiment, the housing 12 is made of a flexible 60 Shore A durometer silicone rubber, which allows surgeons to pivot the light blocking shield 28 to enable unhindered scope acceptance to the light cable and visibility of a proper scope connection (FIG. 10B). Upon disconnection of the scope 44 from the light cable 48, the shield 28 with the thermal insulator disc 16 rebounds back to its original position where the intense light is blocked (FIG. 10D).

Figure 11:
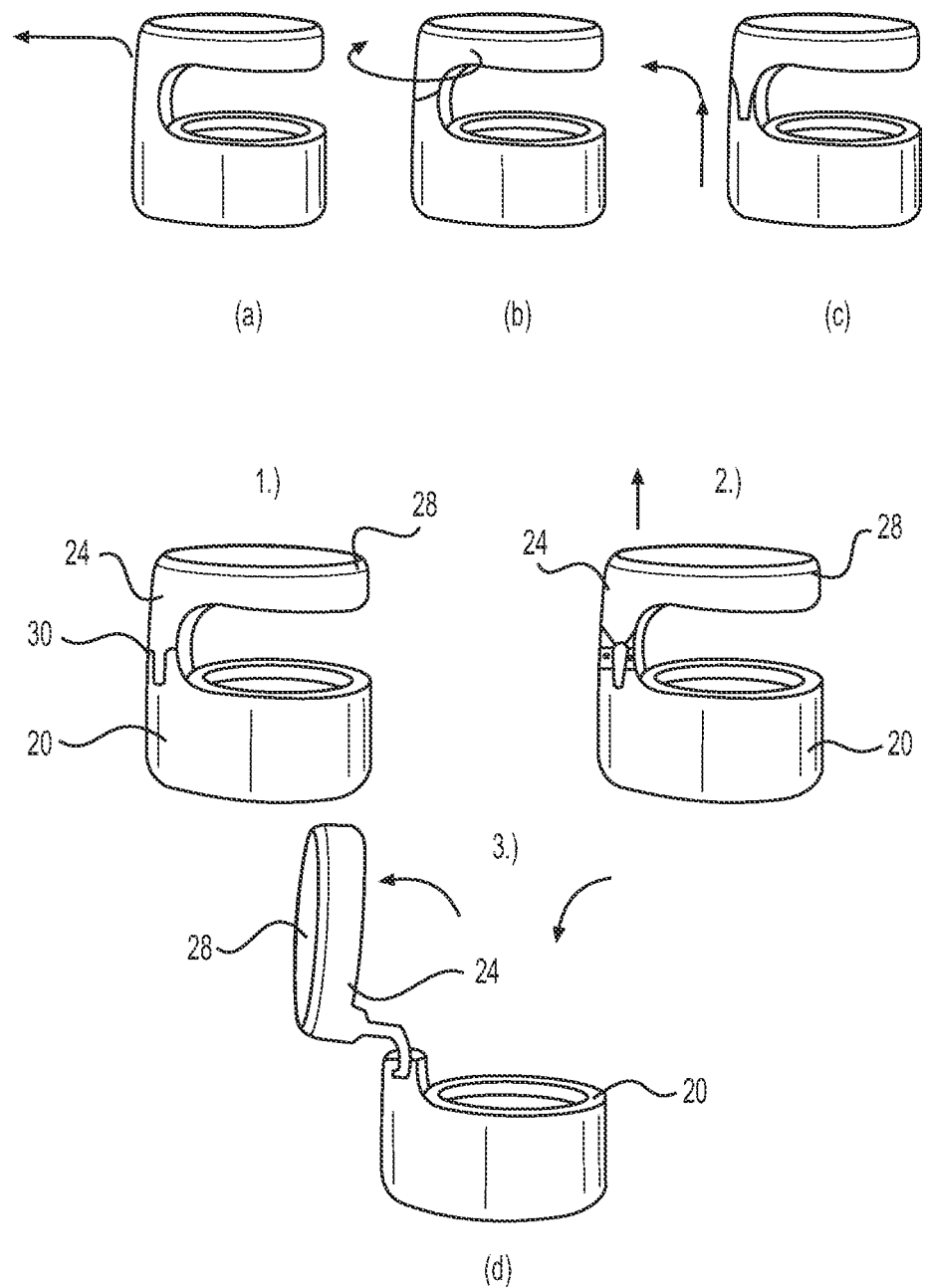
FIGS. 11(a)-(d) illustrate various articulation modalities of the bridge portion for how the bridge can function and displace the shield to promote connection of according to principles of the present invention.

FIGS. 11(a)-(d) illustrate various articulation modalities of the bridge portion for how the bridge can function and displace the shield to promote connection of according to principles of the present invention. FIG. 11(a) illustrates that the bridge portion can flex away from the light emitting tip to allow the shield portion to "flip" up and away from the light emitting tip. FIG. 11(b) illustrates that the bridge can be "twisted" to allow the shield to be "rotated" away from the light emitting tip. FIG. 11(c) illustrates that the bridge can be hinged or pivoted to allow the shield to "flip" up and away from the light emitting tip. As illustrated in FIG. 11(d) a variety of configurations for a hinge or pivot 30 can be utilized to allow for the shield portion to be tilted away from the light emitting tip. For example, the formation of the elastomer forming the bridge portion can be made thinner in appropriate location to all for cross-sectional deformation that would thus create a living hinge. Other motions of the shield portion with respect to the light emitting tip (not shown) are possible either by creating a traditional mechanical hinge, pivot or other translation mechanism, or by varying the type and thickness of elastomer or material making up the housing.

Additional embodiments of the light cable cap according to principles of the present inventions are illustrated in FIGS. 12-15.

Figure 12A:
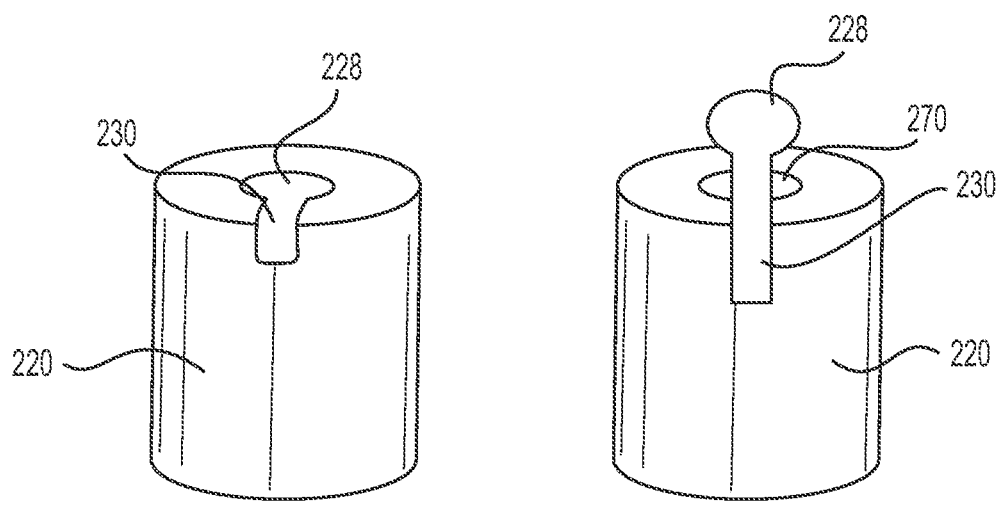
FIGS. 12A and 12B illustrates a "pitcher" and a "can" design in which the light blocking portion can be manually actuated to accommodate the scope.
Figure 12B:
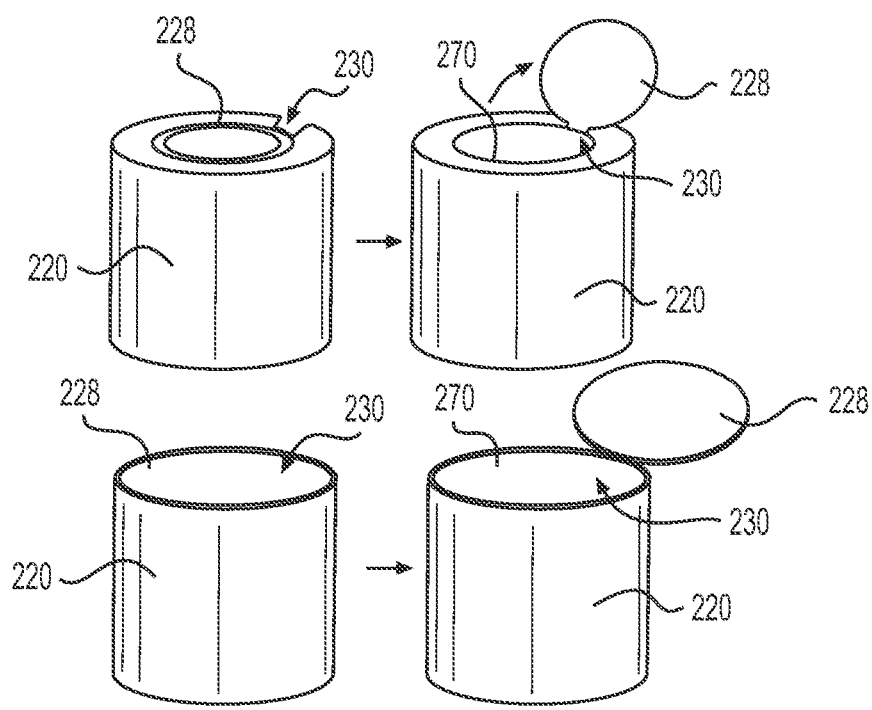

FIGS. 12A and 12B illustrates a "pitcher" or "can" design in which the light blocking portion can be manually actuated to accommodate the scope. The blocking feature returns to place when the scope is removed. As illustrated in FIG. 12, the "ring portion" is a substantially cylindrical housing 220 that can be fitted over the light cable tip (not shown). A shield 228 is coupled to the cylindrical housing 220 via a tether or living hinge 230. The shield 228 can include a separate thermal insulator (not shown). The tether 230 allows the shield 228 to hinge, activate or articulate the shield to and from a light port/opening/orifice 270 at the top of the cylindrical housing 220. FIG. 12B illustrates additional variations of the lid design that can be actuated or manually opened to allow for a connection to a scope. All return back to block the fiber optics when the scope is disconnected.

Figure 13:
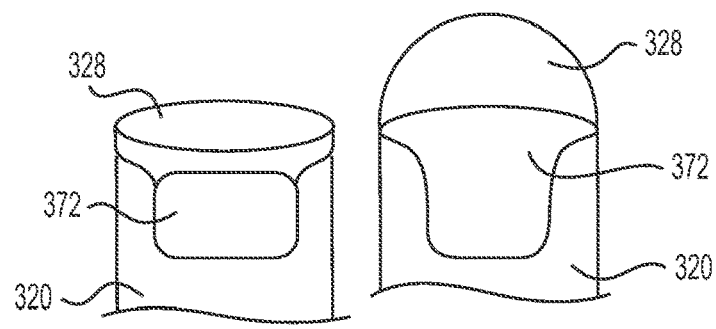
FIG. 13 illustrates a "side port" design that includes a lid feature as well as a gap or port located on the side of the connector.

FIG. 13 illustrates a "side port" design that includes a lid feature 328 as well as a gap or port 372 located on the side of the connector housing 320. The gap or port 372 allows viewing. The lid 328 is wedged open by inserting the scope connector/light tip (not shown) into the gap 372 and manually rotating into the correct orientation. Upon disconnection, the lid 328 closes, blocking the fiber optics.

Figure 14:
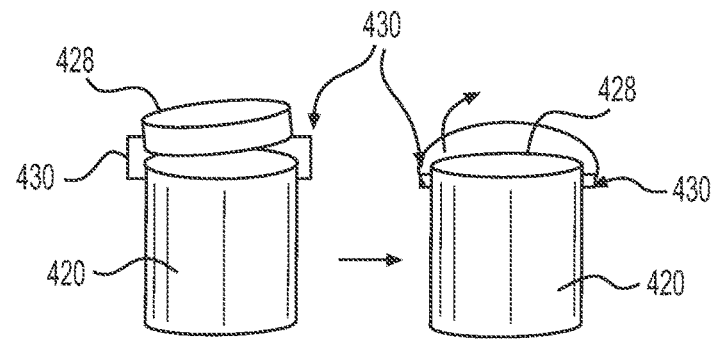
FIG. 14 illustrates a "bucket handle lid" design in which the user to rotate the lid over to the side of the device before connecting the scope.

FIG. 14 illustrates a "bucket handle lid" design in which the user rotates the lid 428 over to the side of the device housing 420 before connecting the scope (not shown). The lid itself may include singular or multiple bridges or arms 430 for articulation and/or multiple articulation points to facilitate movement of the shield away from the light emitting tip and returning it over the light emitting tip when the scope is removed. The bridge(s)/arm(s) 430 may be arranged evenly or unevenly around the shield 428 and housing 420 that provide the mechanism for the shield to rotate over the scope for connection. The shield/lid 428 may include a thermal insulator, as in the other described embodiments, or the thermal insulator may be separate from the shield/lid portion 428. After disconnection, the lid returns to the top, blocking the fiber optics.

Figure 15:
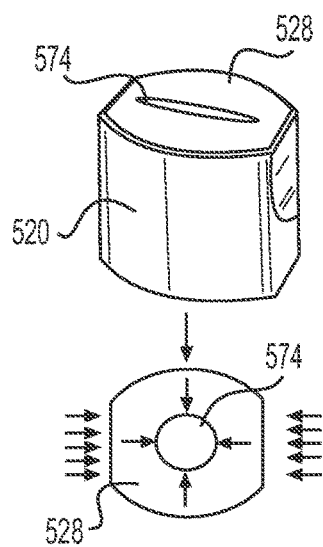
FIG. 15 illustrates a "coin pouch" design with an elliptical slit with flat sides perpendicular to the long axis of the slit.

FIG. 15 illustrates a "coin pouch" design with an elliptical slit 574 in a top face 528 of the light cable cap housing 520. The slit has flat sides perpendicular to the long axis of the slit. The slit may also be linear. When compressed on the flat sides, the device's slit changes shape to a circle or other appropriately shaped gap allowing for the connection of a scope. After disconnection and release of any external forces, the device returns to the same slit shape on the top face, blocking the fiber optic light.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A cap for a light source, the light source having a thermal energy emission range capable of damaging a surrounding environment, the cap comprising: a ring comprising a deformable inner arc defining an opening capable of expansion from and return to an original arc; a shield, the ring separated from the shield by a predetermined distance; and a bridge reboundingly connected at one end to the ring and extending from the ring to the shield and connected at another end to the shield, wherein the bridge has a resting state wherein the shield overlaps the opening; and a thermal insulator embedded in the shield, wherein the thermal insulator comprises a high temperature resistant material different from a material forming the shield.

2. The cap of claim 1, wherein the bridge comprises a flexible material.

3. The cap of claim 1, wherein at least one of the bridge, the shield, and the ring comprises a flexible material.

4. The cap of claim 1, wherein the ring, the shield and the bridge constitute a housing having cylindrical profile.

5. The cap of claim 4, wherein an exterior surface of the housing has a frustoconical profile.

6. The cap of claim 1, wherein the ring is configured to mate over an end of a light source cable.

7. The cap of claim 1, wherein an interior surface of the ring is configured to fit over and abut a light emitting tip of the light source.

8. The cap of claim 1, wherein at least one of the ring, the shield and the bridge comprises silicone.

9. The cap of claim 1, wherein at least one of the ring, the shield and the bridge comprises a flexible silicone rubber having a durometer in the range of Shore 30 A to 100 A.

10. The cap of claim 9, wherein silicone rubber has a durometer of Shore 60 A.

11. The cap of claim 1, further comprising a recess in an upper surface of the shield.

12. The cap of claim 11, wherein the recess extends through the shield to the thermal insulator.

13. The cap of claim 1, further comprising a recess in a surface of the shield closest to the ring portion, wherein the recess is configured to expose the thermal insulator to the light source.

14. The cap of claim 1, wherein the high temperature resistant material is ceramic.

15. The cap of claim 1, wherein the high temperature resistant material is glass-filled silicone.

16. The cap of claim 1, wherein the ring is configured to couple to a light source cable by a friction fit.

17. The cap of claim 1, wherein the ring, the bridge, and the shield are a unitary body.

18. The cap of claim 1, wherein the bridge comprises polypropylene.

19. The cap of claim 1, wherein the high temperature resistant material has a thermal resistivity is 0.02 (m·K)/W.

20. The cap of claim 1, wherein the ring comprises a circular band, wherein at least a portion of an inner surface of the ring comprises the deformable inner arc.

21. The cap of claim 1, wherein the ring comprises elastic material deformable to rebound to a resting state.

22. A cap for a light source, the light source having a thermal energy emission range capable of damaging a surrounding environment, the cap comprising: a ring comprising a deformable inner arc defining an opening capable of expansion from and return to an original arc; a shield, the ring separated from the shield by a predetermined distance; and a bridge reboundingly connected at one end to the ring and extending from the ring to the shield and connected at another end to the shield, wherein the bridge has a resting state wherein the shield overlaps the opening; a thermal insulator in the shield, wherein the thermal insulator comprises a high temperature resistant material different from a material forming the shield; and wherein material of the shield surrounds the thermal insulator.

* * * * *